United States Patent
Hyde-DeRuyscher

(10) Patent No.: US 11,478,463 B2
(45) Date of Patent: *Oct. 25, 2022

(54) MAST CELL STABILIZERS FOR TREATMENT OF CHRONIC INFLAMMATORY CONDITIONS

(71) Applicant: Emergo Therapeutics, Inc., Durham, NC (US)

(72) Inventor: Robin Parish Hyde-DeRuyscher, Chapel Hill, NC (US)

(73) Assignee: Emergo Therapeutics, Inc., Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/341,277

(22) PCT Filed: Oct. 18, 2017

(86) PCT No.: PCT/US2017/057078
§ 371 (c)(1),
(2) Date: Apr. 11, 2019

(87) PCT Pub. No.: WO2018/075574
PCT Pub. Date: Apr. 26, 2018

(65) Prior Publication Data
US 2020/0215049 A1    Jul. 9, 2020

Related U.S. Application Data

(60) Provisional application No. 62/409,557, filed on Oct. 18, 2016.

(51) Int. Cl.
*A61K 31/4535* (2006.01)
*A61K 9/00* (2006.01)

(52) U.S. Cl.
CPC ........ *A61K 31/4535* (2013.01); *A61K 9/0019* (2013.01); *A61K 9/0024* (2013.01); *A61K 9/0043* (2013.01); *A61K 9/0048* (2013.01); *A61K 9/0053* (2013.01)

(58) Field of Classification Search
CPC ................................................ A61K 31/4535
See application file for complete search history.

(56) References Cited

U.S. PATENT DOCUMENTS

| | | |
|---|---|---|
| 6,207,683 B1 | 3/2001 | Aberg et al. |
| 6,207,684 B1 | 3/2001 | Aberg |
| 7,226,934 B1 | 6/2007 | Aberg et al. |
| 8,557,846 B1 | 10/2013 | Aberg et al. |
| 9,138,431 B2 | 9/2015 | Aberg et al. |
| 9,333,199 B2 | 5/2016 | Aberg et al. |
| 9,345,697 B2 | 5/2016 | Aberg et al. |
| 10,160,796 B2* | 12/2018 | Hyde-DeRuyscher ............ C07K 16/1018 |
| 10,494,420 B2* | 12/2019 | Hyde-DeRuyscher ............ A61P 43/00 |
| 10,501,527 B2 | 12/2019 | Hyde-DeRuyscher et al. |
| 10,787,502 B2* | 9/2020 | Hyde-DeRuyscher ............ A61P 43/00 |
| 11,072,648 B2* | 7/2021 | Hyde-DeRuyscher ............ A61K 31/4535 |
| 2003/0118670 A1 | 6/2003 | Smith |
| 2005/0049262 A1 | 3/2005 | Klein et al. |
| 2006/0084695 A1 | 4/2006 | Griffin et al. |
| 2008/0025976 A1 | 1/2008 | Le et al. |
| 2008/0085922 A1 | 4/2008 | Raja et al. |
| 2008/0139531 A1 | 6/2008 | Yanni et al. |
| 2009/0169546 A1 | 7/2009 | Wu et al. |
| 2010/0105734 A1 | 4/2010 | Aberg et al. |
| 2010/0130550 A1 | 5/2010 | Aberg et al. |
| 2010/0166804 A1 | 7/2010 | Penn |
| 2011/0206659 A1* | 8/2011 | Penn .............. A61P 29/00 424/133.1 |
| 2012/0058984 A1 | 3/2012 | Alder et al. |
| 2014/0113936 A1 | 4/2014 | Aberg et al. |
| 2014/0120121 A1 | 5/2014 | Aberg et al. |
| 2014/0205562 A1 | 7/2014 | Wu et al. |
| 2014/0341913 A1 | 11/2014 | Tripp |
| 2015/0224077 A1* | 8/2015 | Gerhart ............ A61K 31/4741 514/456 |
| 2015/0272941 A1 | 10/2015 | Aberg et al. |
| 2016/0046730 A1 | 2/2016 | Ghayur et al. |
| 2016/0193143 A1 | 7/2016 | Aberg et al. |
| 2016/0228426 A1 | 8/2016 | Aberg et al. |
| 2017/0105987 A1* | 4/2017 | Aberg ................ A61K 31/4535 |
| 2018/0072796 A1 | 3/2018 | Hyde-DeRuyscher et al. |
| 2020/0055926 A1 | 2/2020 | Hyde-DeRuyscher et al. |
| 2020/0055927 A1 | 2/2020 | Hyde-DeRuyscher et al. |

FOREIGN PATENT DOCUMENTS

| | | |
|---|---|---|
| CA | 2283663 | 10/1998 |
| CA | 2780453 | 6/2011 |
| CA | 2886194 | 5/2014 |
| CN | 1391475 A | 1/2003 |
| CN | 101990437 A | 3/2011 |

(Continued)

OTHER PUBLICATIONS

Frieri et al. Curr. Allergy Asthma Rep., 2013, vol. 13, pp. 27-32 (Year: 2013).*

(Continued)

*Primary Examiner* — James D. Anderson
(74) *Attorney, Agent, or Firm* — Myers Bigel, P.A.

(57) ABSTRACT

The present invention relates to methods for treating chronic inflammatory conditions using a mast cell stabilizing compound. The invention further relates to compositions and dosage forms comprising mast cell stabilizing agents.

10 Claims, No Drawings

(56) References Cited

FOREIGN PATENT DOCUMENTS

| EP | 2234629 | | 10/2010 | | |
|---|---|---|---|---|---|
| EP | 2928299 | | 10/2015 | | |
| EP | 2911510 | | 6/2016 | | |
| EP | 3124049 | A1 | 2/2017 | | |
| WO | 9835677 | | 8/1998 | | |
| WO | 9856381 | A1 | 12/1998 | | |
| WO | 0119367 | A1 | 3/2001 | | |
| WO | 2009088570 | | 7/2009 | | |
| WO | 2009142772 | | 11/2009 | | |
| WO | 2010/107525 | | 9/2010 | | |
| WO | 2011068786 | | 6/2011 | | |
| WO | 2014/070696 | | 5/2014 | | |
| WO | 2014066212 | | 5/2014 | | |
| WO | 2014070696 | | 5/2014 | | |
| WO | 2015020878 | A1 | 2/2015 | | |
| WO | 2015147296 | A1 | 10/2015 | | |
| WO | WO-2016011254 | A1 * | 1/2016 | ........... | A61K 31/352 |
| WO | 2016019246 | A1 | 2/2016 | | |
| WO | 2016130968 | | 8/2016 | | |
| WO | 2017035418 | | 3/2017 | | |

OTHER PUBLICATIONS

Singh et al. BMC Gastroenterology (2015) 15:47, 8 pages (Year: 2015).*
Rintala et al. J. Pediatr. Surg., 2001, vol. 36, pp. 1032-1035 (Year: 2001).*
Kobayashi et al. Japanese Journal of Pharmacology, 2002, vol. 90, No. 1, pp. 7-11 (Abstract attached) (Year: 2002).*
International Search Report and Written Opinion corresponding to International Application No. PCT/US2017/057078 dated Feb. 7, 2018.
U.S. Appl. No. 15/697,835, filed Sep. 7, 2017; Office Action dated Jun. 12, 2019.
U.S. Appl. No. 16/664,037, filed Oct. 25, 2019, Office Action dated Jan. 30, 2020.
U.S. Appl. No. 15/697,835, filed Sep. 7, 2017; Office Action dated Dec. 15, 2017.
U.S. Appl. No. 15/816,461, filed Nov. 17, 2017; Office Action dated Dec. 15, 2017.
U.S. Appl. No. 16/192,385, filed Nov. 15, 2018; Office Action dated Dec. 31, 2018.
International Preliminary Report on Patentability corresponding to International Application No. PCT/US2017/050409 dated Mar. 21, 2019.
International Preliminary Report of Patentability corresponding to International Application No. PCT/US2017/057078, dated May 2, 2019.
Notification of Transmittal of the International Search Report and the Written Opinion of the International Searching Authority, or the Declaration corresponding to International Application No. PCT/US2017/050409 dated Dec. 14, 2017.
Graham, Amy C., "The Role of Mast Cells During Influenza A Virus Infection", Dissertation Apr. 2015 (299 pages).
Graham et al. "Mast cells and influenza A virus: association with allergic responses and beyond", Frontiers in Immunology 6:1-12(2015).
Gwathmey et al. "Neurologic indications for therapeutic plasma exchange: an update.", J Clin Apher. 26(5):261-8 (2011) Abstract Only.
Han et al. "The therapeutic effects of sodium cromoglycate against influenza A virus H5N1 in mice", Influenza and Other Respiratory Viruses 10(1):57-66 (2016).
Hu et al. "Mast Cell-Induced Lung Injury in Mice Infected with H5N1 Influenza Virus", Journal of Virology 8(6):3347-3356 (2012).
Liu et al. "The cytokine storm of severe influenza and development of immunomodulatory therapy", Cellular & Molecular Immunology 13:3-10 (2016).
Negro-Alvarez et al. "Antiallergic properties of antihistamines.", Allergol Immunopathol (Madr.) 24(4):177-83 (1996).
Nishibori et al. "[Regulation of cytokine production by histamine through H2-receptor stimulation].", Nihon Yakurigaku Zasshi 118(1):29-35 (2001) Abstract Only.
O'Brien et al. "Oseltamivir for Treatment of Influenza in Healthy Adults: Pooled Trial Evidence and Cost-Effectiveness Model for Canada", Value in Health 6(2):116-125 (2003).
Patel et al. "Use of therapeutic plasma exchange as a rescue therapy in 2009 pH1N1 influenza—An associated respiratory failure and hemodynamic shock", Pediatric Critical Care Medicine 12(2):1-3 (2011).
St. John "Influence of Mast Cells on Dengue Protective Immunity and Immune Pathology", PLOS Pathogens 9(12):e1003783 (2013).
Teijaro et al. "Mapping the innate signaling cascade essential for cytokine storm during influenza virus infection", PNAS 111(10):3799-3804 (2014).
Yang et al. "The role of mast cells in ischemia and reperfusion injury", Inflamm. Res. 63:899-905 (2014).
Extended European Search Report corresponding to European Application No. 17849505.7 dated Apr. 2, 2020.
U.S. Appl. No. 16/192,385, filed Nov. 15, 2018; Office Action dated Apr. 29, 2019.
U.S. Appl. No. 15/816,461, filed Nov. 17, 2017; Office Action dated Jun. 8, 2018.
U.S. Appl. No. 16/192,385, filed Nov. 15, 2018; Office Action dated Sep. 12, 2019.
"Search Report and Written Opinion corresponding to Singapore Application No. 11201902056P dated Jun. 26, 2020".
"Extended European Search Report corresponding to European Application No. 17861667.8 dated May 11, 2020".
Ambrosini, Roberta, et al., "Inflammatory chronic disease of the colon: How to image", European Journal of Radiology 61:442-448 (2007).
König, Katrin, et al., "Cytokine profiles in nasal fluid of patients with seasonal or persistent allergic rhinitis", Allergy Asthma Clin Immunol 11:26 (2015).
Kotas, Maya E., et al., "Homeostasis, Inflammation, and Disease Susceptibility", Cell 160(5):816-827 (2015).
Tyurin, Yury A., et al., "Cytokine Profile of Patients with Allergic Rhinitis Caused by Pollen, Mite, and Microbial Allergen Sensitization", Journal of Immunology Research, vol. 17, Article ID 3054217 (2017) (7 pages).
Valent, Peter, et al., "Definitions, Criteria and Global Classification of Mast Cell Disorders with Special Reference to Mast Cell Activation Syndromes: A Consensus Proposal", Int Arch Allergy Immunol 157:215-225 (2012).
"Office Action corresponding to Mexican Application No. MX/A/2019/002781 dated Jun. 4, 2021".
U.S. Appl. No. 15/697,835, filed Sep. 7, 2017; Office Action dated Jun. 18, 2018.
"U.S. Appl. No. 16/664,039, filed Oct. 25, 2019: Office Action dated Feb. 17, 2021".
"Office Action corresponding to Indian Application No. 201917010051 dated Dec. 17, 2020".
"Office Action corresponding to Indonesian Application No. PID201902737 dated Mar. 18, 2021".
"Office Action corresponding to Russian Application No. 2019110150 dated Dec. 18, 2020".
Bernstein, Jonathan A, et al., "Clinical characteristics of chronic rhinitis patients with high vs low irritant trigger burdens", Ann Allergy Asthma Immunol 109:173-178 (Jun. 22, 2012).
Coruzzi, Gabriella, et al., "Strain-dependent effects of the histamine H4 receptor antagonist JNJ7777120 in a murine model of acute skin inflammation", Experimental Dermatology 21:32-37 (Oct. 11, 2011).
Eifan, A. O, et al., "Pathogenesis of rhinitis", Clinical & Experimental Allergy 46:1139-1151 (Sep. 2016).
Galli, Stephen J, et al., "Mast Cells as "Tunable" Effector and Immunoregulatory Cells: Recent Advances", Annu. Rev. Immunol. 23:749-86 (Jan. 7, 2005).
Giannetti, Arianna, et al., "Mast Cell Activation Disorders", Medicina 57:124 (Jan. 30, 2021) 13 pages.

(56) References Cited

OTHER PUBLICATIONS

Plaisance, Karen I., et al., "Antipyretic Therapy: Physiologic Rationale, Diagnostic Implications, and Clinical Consequences", Arch. Intern. Med. 160(4):449-456 (2000).
Vandenplas, O., et al., "EAACI position paper: irritant-induced asthma", Allergy 69:1141-1153 (May 16, 2014).
Zhang, Xiang-Yan, et al., Hemophagocytic Lymphohistiocytosis Induced by Severe Pandemic Influenza A (H1N1) 2009 Virus Infection: A Case Report Case Rep Med. 2011; 2011: 951910 (3 pages).
"Office Action corresponding to Chinese Application No. 201780068796.6 dated Jun. 23, 2021".
"Office Action corresponding to Russian Application No. 2019110150 dated Apr. 29, 2021".
"Office Action corresponding to Brazilian Application No. 112019004496-5 Sep. 15, 2021".
"Office Action corresponding to Chinese Application No. 2017800687966 dated Dec. 8, 2021".
"Office Action corresponding to Indonesian Application No. PID201902737 dated Oct. 5, 2021".
"Office Action corresponding to Japanese Application No. 2019-535191 dated Aug. 3, 2021".
"Office Action corresponding to Japanese Application No. 2019-542351 dated Sep. 27, 2021".
"Office Action corresponding to Saudi Arabian Application No. 519401254 dated Oct. 28, 2021".
"Written Opinion corresponding to Singapore Application No. 11201902056P dated Mar. 8, 2022".
"Office Action corresponding to Israeli Application No. 265,208 dated Mar. 17, 2022".
"Office Action corresponding to European Application No. 17849505.7 dated Feb. 23, 2022".
"Examination Report corresponding to European Application No. 17861667.8 dated Apr. 4, 2022".
"Office Action corresponding to Japanese Application No. 2019-542351 dated Apr. 27, 2022".
Nakabayashi, Atsuhiro, et al., "Three Cases of Mastocytosis", Skin Research 41(2):165-169 (1999).
"Office Action corresponding to Chinese Application No. 2017800687966 dated May 27, 2022".
"Office Action corresponding to Australian Application No. 2017325010 dated Jun. 24, 2022".
"Office Action corresponding to Japanese Application No. 2019-535191 dated Jul. 6, 2022".
"Office Action corresponding to Saudi Arabian Application No. 519401254 dated Jul. 31, 2022".

\* cited by examiner

MAST CELL STABILIZERS FOR TREATMENT OF CHRONIC INFLAMMATORY CONDITIONS

STATEMENT OF PRIORITY

This application is a 35 U.S.C. § 371 national phase application of PCT Application PCT/US2017/057078 filed Oct. 18, 2017, which claims the benefit of U.S. Provisional Application Ser. No. 62/409,557, filed Oct. 18, 2016, the entire contents of each of which are incorporated by reference herein in its entirety.

FIELD OF THE INVENTION

The present invention relates to methods for treating chronic inflammatory conditions using a mast cell stabilizing compound. The invention further relates to compositions and dosage forms comprising mast cell stabilizing agents.

BACKGROUND OF THE INVENTION

Mast cells are a unique hematopoietic cell that is resident only in tissue and not in the blood stream. They are sentinels, constantly on the lookout for invading organisms, toxic molecules and tissue damage. When mast cells encounter such pathogens or damage, they release a flood of mediators; these mediators are a mix of small molecule effectors (such as histamine), proteases, lipid-derived signaling molecules (prostaglandins) and cytokines. The process of releasing these mediators is generically termed "degranulation."

The release of mediators via degranulation results in the recruitment of a wide variety of immune cells to the site of mediator release to fight the offending intruder. This process also induces localized inflammation to restrict the movement of any infection or toxin. A controlled inflammatory response to foreign bodies enables the body to prevent the spread of toxins to neighboring tissues, limiting damage to one area and is desirable. Once the toxin has been neutralized, the normal course is for the body to begin an active resolution of inflammation response (ROI). This results in an egress of recruited immune cells from the injured tissue, tissue remodeling, a reduction in swelling and finally complete healing.

In some cases, this normal course of a proportional inflammatory response, followed by resolution is not followed. This can result in either a chronic state of inflammation or an overly robust mediator response that is out of proportion to the invading event. In chronic inflammation, the ongoing release of mediators that induce a low level inflammatory state has been implicated in a large variety of medical conditions including diverse therapeutic areas like neurologic, pulmonary/cardiology, immune dysfunction, cancer, allergic disorders, metabolic and psychiatric/neurocognitive disorders. The symptoms can be a direct result of mediator release (as in mastocytosis and mast cell activation syndrome) or in other cases the result of the damage caused by chronic inflammation (for example atherosclerosis and Hashimoto's thyroiditis). While the symptoms for these diseases are very diverse and the pathology observed very different, at the base of the problem is an ongoing inflammatory state that allows the condition to persist and progress. This condition can be due to inappropriate release of inflammatory mediators from mast cells.

Current treatments for chronic inflammatory states do not generally do anything to ameliorate the ongoing production of inflammatory mediators that perpetuate this condition. These conditions are usually treated by administering antagonists to one specific inflammatory mediator. In most of these chronic diseases, the problem is the ongoing production of a dozen or more inflammatory mediators. Thus, trying to reverse the symptoms by blocking one mediator is often ineffective.

In many of these chronic conditions, treating the inflammation with corticosteroids is effective. Corticosteroids are very powerful down regulators of the innate and adaptive immune system. "Turning off" all aspects of the immune response for an extended period of time does not allow the clearance of pathogens and thus infection is a serious concern for patients who need to remain on long term systemic steroid treatment. In addition, corticosteroids have wide ranging pleiotropic effects on many aspects of biology and should be avoided long term if possible. Thus, a balance must be struck between an overly robust immune response and too little of a response.

Mast cell activation disorders are characterized by a chronic over release of inflammatory mediators from mast cells. These disorders can be broadly divided into two groups. In the first there is an overabundance of mast cells and the disorders are typified by systemic mastocytosis and mast cell leukemia. In the second group (mast cell activation syndrome or MCAS), the number of mast cells remains normal, however, they release mediators in an ongoing process, resulting in symptoms including urticaria, angioedema, flushing, nausea, vomiting, diarrhea, abdominal cramping, hypotensive syncope or near syncope, tachycardia, wheezing, conjunctival infection, pruritus, and nasal stuffiness. These conditions are often misdiagnosed as postural orthostatic tachycardia syndrome (PoTS), bad allergies, inflammatory bowel disease or psychosomatic illness among others. The name "MCAS" was coined in 2007 and diagnostic criteria for the syndrome is still evolving.

Mast cell stabilizers such as ketotifen and cromolyn (sodium cromoglycate) have been shown to inhibit mast cell degranulation and the resulting release of mediators such as histamine, tumor necrosis factor (TNF)-α, prostaglandins, leukotrienes, interleukins and other cytokines. These effects may not be limited to mast cells and might have a broader effect of reducing inflammatory cytokine release in multiple cell types. These compounds, however, do not impact the adaptive immune system and allow antibody based clearance of foreign bodies from the body to continue essentially as normal. Both of these compounds are used to treat chronic conditions. Cromolyn was discovered and used as an inhaled treatment for asthma. Ketotifen was discovered as an H1 antihistamine and is used extensively in eye drop formulations to treat eye inflammation. It was also developed as an oral treatment for asthma, although this seems to take several weeks for it to have significant impact on chronic asthma.

The present invention overcomes shortcomings in the art by providing compositions and methods for treating mast cell disorders, chronic inflammation, and disorders associated therewith.

SUMMARY OF THE INVENTION

The present invention relates to the development of treatments to down regulate mast cell activation in order to intervene successfully in cases of chronic inflammation. The present invention provides a more effective way to aid the body in balancing inhibition of an overly robust immune response and providing too little of a response to provide a treatment that allows the ongoing inflammation to be addressed while still allowing the body to respond to infections. This can be accomplished with a treatment regime that down regulates the innate immune system and allows the adaptive immune system to remain active, protecting the body from pathogens.

Accordingly, as one aspect, the invention provides a method of treating, ameliorating, or preventing chronic inflammation in a subject in need thereof, comprising administering to the subject a therapeutically effective or prevention effective amount of a mast cell stabilizing compound, thereby treating, ameliorating, or preventing the chronic inflammatory state.

The invention additionally relates to the use of a mast cell stabilizing compound for treating, ameliorating, or preventing chronic inflammation in a subject in need thereof.

The invention also relates to a pharmaceutical composition comprising norketotifen and a pharmaceutically acceptable carrier.

The invention further relates to dosage forms comprising the pharmaceutical compositions of the invention.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, +5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the time period of symptoms is less than what would occur in the absence of the present invention.

A "treatment effective" or "therapeutically effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

"Chronic inflammation," as used herein, refers to long-term inflammation lasting at least one month and often lasting several months or years. Chronic inflammation can be due to many different factors, including without limitation, failure to eliminate whatever was causing an acute inflammation, an autoimmune response to a self antigen, a chronic irritant of low intensity, non-degradable pathogens, persistent foreign bodies, infection with some types of viruses, or an overactive immune system. Several diseases and conditions may be associated with chronic inflammation, including without limitation, asthma, chronic peptic ulcer, tuberculosis, rheumatoid arthritis, chronic periodontitis, ulcerative colitis, Crohn's disease, chronic sinusitis, psoriasis, chronic tissue injury, and chronic active hepatitis.

As used herein, the term "mast cell activation disease" (MCAD) or "mast cell activation syndrome" (MCAS), refers to an immune reaction consisting of elevated levels of various cytokines caused by inappropriate, overactive release of these mediators from mast cells or other cells in the immune system. In some cases, these elevated mediator levels are measurable in serum or urine, however, symptoms may be present without a detectable increase in levels. Nonetheless, these symptoms are still caused by an excess release of mediators. Symptoms of MCAS may include urticaria, angioedema, flushing, nausea, vomiting, diarrhea, abdominal cramping, hypotensive syncope or near syncope, tachycardia, wheezing, conjunctival injection, pruritus, nasal stuffiness among others.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's Pharmaceutical Science; $21^{st}$ ed. 2005). Exemplary pharmaceutically acceptable carriers for the compositions of this invention include, but are not limited to, sterile pyrogen-free water and sterile pyrogen-free physiological saline solution.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention is designed to address physical symptoms caused by a chronic overabundance of inflammatory mediators produced by mast cells while minimizing the impact of these treatments on the adaptive immune system and central nervous system. This is accomplished by using a compound that does not reduce the adaptive immune response or cause drowsiness.

Mast cells are the resident sentinels that detect and react to an initial invasion by a pathogen. Upon sensing a foreign body or injury (bacteria, virus, molecule, or other insult) mast cells release a series of chemical mediators that include histamine, prostaglandins, and cytokines among others. This release of mediators calls in the first responders of the immune system, including T cells, to address the problem. Mast cells continue to release cytokines which spread systemically and continue to recruit more immune cells to the infection. These attracted cells also release cytokines to ramp up the immune response. The result can be a self-reinforcing loop that requires an active process to turn off the inflammatory process. In some instances, this process is not down regulated and continues, resulting in a chronic inflammatory state. The multiple mediators released present a challenge to treating this condition as it makes the target multifaceted. Blocking a single mediator is often not effective at resolving the inflammatory state. To effectively return the inflammatory state to a neutral one, the release of mediators must be prevented.

There are multiple mast cell stabilizing compounds known in the art. Examples of mast cell stabilizing compounds include, without limitation, ketotifen, norketotifen, cromolyn, nedocromil, quercetin, pemirolast, olopatadine, ebastine and carebastine. In some embodiments, the methods of the invention use the ketotifen metabolite norketotifen or a pharmaceutically acceptable salt thereof. The present invention is based in part on previously unrealized advantages of norketotifen vs. ketotifen as a treatment for mast cell disorders. There are several limitations of ketotifen as a treatment for these disorders. First, it causes extreme drowsiness in many patients and limits the dosage utilized by all patients. This limitation in turn reduces ketotifen's ability to act as an effective mast cell stabilizer in both acute and chronic timelines. In contrast, norketotifen does not cause drowsiness, allowing it to be utilized by many more patients on a prophylactic basis and still allow them to maintain a normal, productive schedule throughout the day. In addition, norketotifen can be used at higher dosages, allowing it to be a more effective mast cell stabilizer, reducing symptoms to a greater degree than ketotifen. Finally, norketotifen has a longer half-life than ketotifen, allowing the dosing regimens to be more convenient.

In some embodiments, the mast cell stabilizing compound is administered concurrently with an additional therapeutic agent, e.g., an agent suitable for treatment of inflammation or an agent suitable for treatment of the underlying disease or condition that is causing the chronic inflammation. Examples of additional therapeutic agents include, without limitation, anti-inflammatory agents such as H1-antihistamines (e.g., cetirizine), H2-antihistamines (e.g., ranitidine, famotidine), antileukotrienes (e.g., montelukast, zileuton), and nonsteroidal anti-inflammatory drugs. The mast cell stabilizing compound and the additional therapeutic agent may be administered to the subject in the same composition or in separate compositions, e.g., administered concurrently. The additional therapeutic agent can be delivered to the subject on a different schedule or by a different route as compared to the mast cell stabilizing compound. The additional therapeutic agent can be any agent that provides a benefit to the subject.

The compounds of the invention may be administered to the subject as needed to treat a disease, disorder, or condition. The compound can be administered continuously or intermittently. In one embodiment, the compound is administered to the subject more than once a day or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The compounds of the invention can be delivered to the subject by any suitable route, e.g., oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration.

The mast cell stabilizing compound may be in an inhaler for delivery to airways.

A mast cell stabilizing compound may be delivered over several days, likely more than 3 days, in order to reduce the impact of chronic mediator release. A time-release microsphere approach could also be used to deliver the mast cell stabilizing compound and ensure that it is present for an extended time, even with only one dose. Shiny et al. (*Int. J. Pharm. Investig.* 3(3):119 (2013)) is an example of an approach for up to 30-day continuous delivery.)

The compounds are delivered to the subject at a dose that is effective to treat the disorder. The effective dosage will depend on many factors including the gender, age, weight, and general physical condition of the subject, the severity of the disorder, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* ($21^{st}$ ed. 2005)). In one embodiment, the mast cell stabilizing compound is administered at a dose of about 0.001 to about 100 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10 20, 30, 40, 50, 60, 70, 80, 90, 100, 200, 300, 400, or 500 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. For norketotifen the dosing range may be from about 0.05 mg/kg to about 10 mg/kg, e.g., from about 0.1 mg/kg to about 1 mg/kg. The present invention encompasses every sub-range within the cited ranges and amounts.

Twice daily dosing of ketotifen at 2 mg per dose is the current approach used for mast cell disorders. It takes at least 2.5 days to approach a steady state level near 2 ng/ml. If the 4 mg/day dosing is taken in one dose, it surpasses the steady state level rapidly, but each day the overall level drops significantly and falls below 2 ng/ml. If a time release approach is used with the first dose doubled to 8 mg, the 2 ng/ml level is achieved quickly, the overall level does not go too high and a consistent dose above 2 ng/ml is maintained. Thus, the use of a time release approach, optionally with an increased initial dose, allows for a rapid increase of systemic drug levels that are maintained throughout the treatment. This same approach would also be useful for norketotifen to achieve therapeutically effective levels faster and to reduce the number of daily doses required to maintain this level.

Some medications are delivered subcutaneously or intramuscularly to ensure the availability of compounds that are not readily absorbed by other administration routes. This method also has the advantage of speed and being practical in hospitals, physician's offices, pharmacies and the home. There are many auto injector systems available that would facilitate self-injection of therapeutic doses of the combination of the invention. As it is likely that the dosing schedule will be for an extended period of time, a system that allows for multiple dosing from a single device (or "pen") would increase convenience and compliance with the needed injection schedule.

For some patients (including children), swallowing tablets or pills is difficult or impossible. In these cases, it may be advantageous to deliver the combination of the invention in an oral liquid formulation. This formulation may deliver the drug combination in a time release mechanism or any other desired delivery profile. This may also be accomplished using a suppository for intra-rectal delivery.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has chronic inflammation or a disease or disorder that can lead to chronic inflammation. The methods of the invention may be used prophylactically to delay the onset of symptoms and/or reduce the severity of symptoms upon onset of chronic inflammation. In other embodiments, the subject used in the methods of the invention is an animal model of chronic inflammation.

The subject can be a subject "in need of" the methods of the present invention, e.g., in need of the therapeutic and/or prophylactic effects of the inventive methods. In some embodiments, the disease, disorder, or condition is not asthma, conjunctivitis, or mastocytosis.

A further aspect of the invention relates to a pharmaceutical composition comprising norketotifen and a pharmaceutically acceptable carrier. The pharmaceutical composition may further comprise an additional therapeutic agent, e.g., an anti-inflammatory agent.

An additional aspect of the invention relates to a dosage form comprising the pharmaceutical composition of the invention. The dosage form may be any dosage form known in the art that is suitable for the methods of the present invention. The dosage form be, without limitation, a solid or liquid oral dosage form, a dosage form for nasal and/or oral inhalation, a dosage form for intravenous administration, a dosage form for transdermal or mucosal administration (e.g., a patch), a dosage form for injection (e.g., subcutaneous or intramuscular), a dosage form for implantation (e.g., a dissolvable formulation or a device such as a pump), or a dosage form for ocular administration.

The compounds of this invention (e.g. norketotifen) include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

Compounds of the invention include those having quaternization of any basic nitrogen-containing group therein. Compounds of the invention further include those comprising one or more isotopes, e.g., deuterium of $^{13}$C.

The discussion herein is, for simplicity, provided without reference to stereoisomerism. Those skilled in the art will appreciate that the compounds of the invention can contain one or more asymmetric centers and thus occur as racemates and racemic mixtures, single optical isomers, individual diastereomers, and diastereomeric mixtures. All such isomeric forms of these compounds are expressly included in the present invention.

Similarly, compounds of the invention containing a double bond can exist in the form of geometric isomers, which can be readily separated and recovered by conventional procedures. Such isomeric forms are included in the scope of this invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

The compounds of the invention described above can be formulated for administration in a pharmaceutical carrier in accordance with known techniques. See, e.g., Remington, *The Science And Practice of Pharmacy* (21$^{st}$ ed. 2005). In the manufacture of a pharmaceutical composition according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a multiparticulate, powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

The term "tablet" as used herein includes, but is not limited to, immediate release (IR) tablets, sustained release (SR) tablets, extended release (ER) tablets, matrix tablets, multilayer tablets, multilayer matrix tablets, delayed release tablets and pulsed release tablets, any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms that may be useful in the practice of the invention include those selected from the group consisting of IR tablets, SR tablets, ER tablets, coated IR tablets, coated SR tablets, coated ER tablets, matrix tablets, coated matrix tablets, multilayer tablets, coated multilayer tablets, multilayer matrix tablets and coated multilayer matrix tablets. In some embodiments, a tablet dosage form is an enteric-coated tablet dosage form. In some embodiments, a tablet dosage form is an enteric-coated extended release tablet dosage form.

The term "capsule" as used herein includes, but is not limited to, IR capsules, SR capsules, ER capsules, coated IR capsules, coated SR capsules, and ER capsules, including delayed release capsules. Capsules may be filled with powders, granules, multiparticulates, tablets, semi-solids, or liquids. In some embodiments, a capsule dosage form is an enteric-coated capsule dosage form. In some embodiments, a capsule dosage form is an enteric-coated extended release capsule dosage form. Capsules may be made of hard gelatin, soft gelatin, starch, cellulose polymers, or other materials as known to the art.

The term "multiparticulate" as used herein means a plurality of discrete particles, microparticles, nanoparticles, pellets, mini-tablets and mixtures or combinations thereof. If the oral form is a multiparticulate capsule, hard or soft gelatin capsules or capsules of other materials can suitably be used to contain the multiparticulate. In some embodiments, a sachet can suitably be used to contain the multiparticulate. In some embodiments, the multiparticulate may be coated with a layer containing rate controlling polymer material. In some embodiments, a multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

In some embodiments, the multiparticulate and one or more auxiliary excipient materials can be compressed into tablet form such as a multilayer tablet. In some embodiments, a multilayer tablet may comprise two layers containing the same or different levels of the same active ingredient having the same or different release characteristics. In some embodiments, a multilayer tablet may contain different active ingredients in each layer. Such a tablet, either single layered or multilayered, can optionally be coated with a controlled release polymer so as to provide additional controlled release properties. In some embodiments, a multiparticulate dosage form comprises a capsule containing delayed release rapid onset minitablets. In some embodiments, a multiparticulate dosage form comprises a delayed release capsule comprising instant release minitablets. In some embodiments, a multiparticulate dosage form comprises a capsule comprising delayed release granules. In some embodiments, a multiparticulate dosage form comprises a delayed release capsule comprising instant release granules.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 0.001 mg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal formulations containing the compound disclosed herein, can be lyophilized to produce a lyophilizate which can be reconstituted with a pharmaceutically acceptable carrier, such as water, to regenerate a liposomal suspension.

In certain embodiments, the dosage form is an extended release dosage form. The dosage form may have a half-life of at least 24 hours. In some embodiments, the extended release dosage form will provide a slower release of the drug over a 24-hour time period such that a consistent, tight range of the drug is available systemically for 24 hours. In certain embodiments, as shown in the example in FIG. 1, the serum level of the compound is kept above 2 ng/mL throughout the treatment period, but at the same time does not rise above 2.5 ng/mL. The dosage form may comprise and/or be coated with a rate controlling polymer material, e.g., hydroxypropyl methylcellulose, a polymer of acrylic or methacrylic acid or their respective esters, or copolymers of acrylic or methacrylic acid or their respective esters.

In any of the above-mentioned embodiments, a controlled release coating (e.g., an enteric coating) may be applied to the final dosage form (capsule, tablet, multilayer tablet, etc.). The controlled release coating may typically comprise a rate controlling polymer material as defined above. The dissolution characteristics of such a coating material may be pH dependent or independent of pH.

The term "rate controlling polymer material" as used herein includes hydrophilic polymers, hydrophobic polymers and mixtures of hydrophilic and/or hydrophobic polymers that are capable of controlling or retarding the release of the compound from a dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly(alkylmethacrylate) and poly (vinyl acetate). Other suitable hydrophobic polymers include polymers and/or copolymers derived from acrylic or methacrylic acid and their respective esters, zein, waxes, shellac and hydrogenated vegetable oils. Particularly useful in the practice of the present invention are poly acrylic acid, poly acrylate, poly methacrylic acid and poly methacrylate polymers. Some of these polymers (e.g., poly methacrylate polymers) can be used as delayed release polymers to control the site where the drug is released.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method of treating or ameliorating chronic inflammation in a subject in need thereof, comprising administering to the subject a therapeutically effective amount of norketotifen or a pharmaceutically acceptable salt thereof, thereby treating or ameliorating the chronic inflammation; wherein the chronic inflammation is due to a pathogen.

2. The method of claim 1, further comprising administering to the subject an additional therapeutic agent.

3. The method of claim 2, wherein the additional therapeutic agent is an anti-inflammatory agent.

4. The method of claim 2, wherein the norketotifen or a pharmaceutically acceptable salt thereof and the additional therapeutic agent are administered in the same composition.

5. The method of claim 2, wherein the norketotifen or a pharmaceutically acceptable salt thereof and the additional therapeutic agent are administered in separate compositions.

6. A method of treating or ameliorating chronic inflammation in a subject in need thereof, comprising administering to the subject a therapeutically effective amount of norketotifen or a pharmaceutically acceptable salt thereof, thereby treating or ameliorating the chronic inflammation;
   wherein the chronic inflammation is due to a viral infection.

7. The method of claim 6, further comprising administering to the subject an additional therapeutic agent.

8. The method of claim 7, wherein the additional therapeutic agent is an anti-inflammatory agent.

9. The method of claim 7, wherein the norketotifen or a pharmaceutically acceptable salt thereof and the additional therapeutic agent are administered in the same composition.

10. The method of claim 7, wherein the norketotifen or a pharmaceutically acceptable salt thereof and the additional therapeutic agent are administered in separate compositions.

* * * * *